(12) United States Patent
Roetzer

(10) Patent No.: US 10,092,371 B1
(45) Date of Patent: Oct. 9, 2018

(54) OCCLUSAL SCULPTING DEVICE

(71) Applicant: Patrick L. Roetzer, Benecia, CA (US)

(72) Inventor: Patrick L. Roetzer, Benecia, CA (US)

( * ) Notice: Subject to any disclaimer, the term of this patent is extended or adjusted under 35 U.S.C. 154(b) by 0 days.

(21) Appl. No.: 15/252,135

(22) Filed: Aug. 30, 2016

(51) Int. Cl.
*A61C 3/02* (2006.01)

(52) U.S. Cl.
CPC .................................... *A61C 3/02* (2013.01)

(58) Field of Classification Search
CPC .................................... A61C 3/02; A61C 3/06
See application file for complete search history.

(56) References Cited

U.S. PATENT DOCUMENTS

| | | | |
|---|---|---|---|
| 4,526,542 A * | 7/1985 | Kochis | A61C 3/02 408/202 |
| 5,779,476 A * | 7/1998 | Roetzer | A61C 3/06 433/165 |
| 6,186,788 B1 * | 2/2001 | Massad | A61C 3/02 433/165 |
| 7,021,933 B2 * | 4/2006 | Caldwell | A61B 17/1673 433/165 |
| 7,845,942 B2 * | 12/2010 | Wilkinson | A61C 1/082 433/214 |
| 2007/0238068 A1 * | 10/2007 | Comfortes | A61C 3/02 433/165 |
| 2009/0162812 A1 * | 6/2009 | Harouni | A61C 3/06 433/166 |

* cited by examiner

*Primary Examiner* — Ralph Lewis
(74) *Attorney, Agent, or Firm* — Theodore J. Bielen, Jr.

(57) ABSTRACT

An occlusal cutting and sculpting device for dental applications utilizing a cutting head having a tapered abrasive surface. The cutting head terminates in first and second end portions. A collar overlies and connects to the first end portion of the cutting head and is constructed with a first surface extending outwardly from the cutting head and a curved second surface adjacent the first surface lying apart from the cutting head.

4 Claims, 4 Drawing Sheets

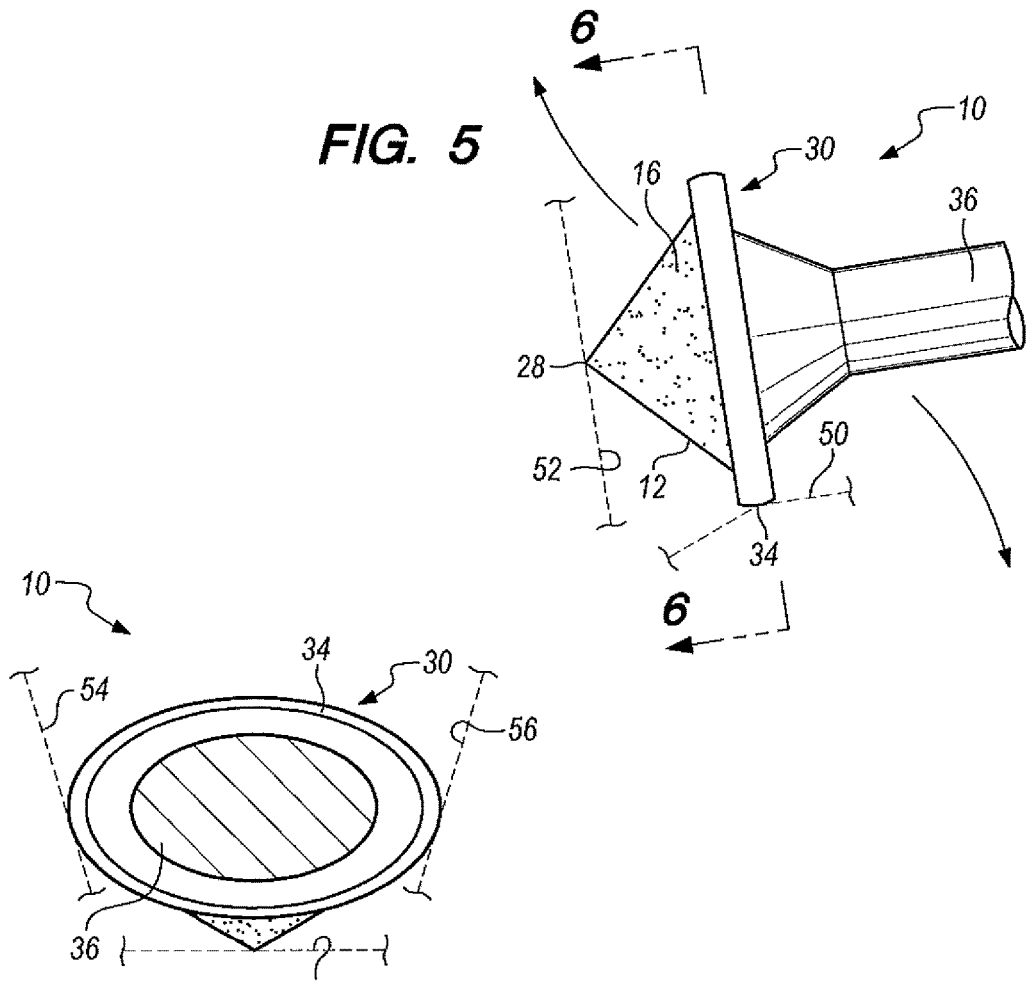
FIG. 5
FIG. 6
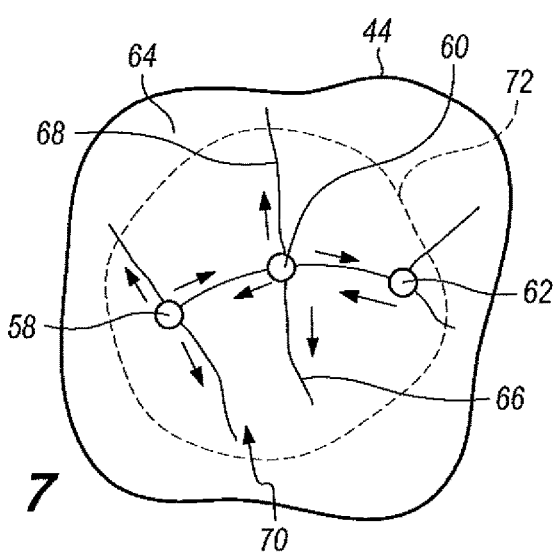
FIG. 7

OCCLUSAL SCULPTING DEVICE

BACKGROUND OF THE INVENTION

The present application relates to a novel and useful occlusal sculpting device which is particularly useful in dental composite restoration applications.

In repairing a decayed tooth, a dental practitioner generally removes the damaged portion of the tooth and fills the same with an enamel compatible material. Typical among such fillings is one composed of a composite resin that is hardened under the influence of blue light. Once hardened, the resin not only fills the cavity left from removal of the damaged enamel, but also extends upwardly from the cavity shaped as a monolithic mass. A dental practitioner must then sculpt the restorative composite material to create an occlusal surface that mimics that of a natural tooth.

In the past, dentists have used enamel cutting burs to achieve this result. However, it has been found that such burs do not create a surface on the tooth that is satisfactory to serve as an occlusal surface and also weaken the restorative material in place in the repaired tooth.

Reference is made to U.S. Pat. No. 5,779,476 which represents an improvement in cutting burs in which the natural cuspal angle of the tooth is provided for in the apex angle of a conical cutting head of the bur. In addition, the bur of the U.S. Pat. No. 5,779,476 included a safe zone consisting of an extension of the conical surface that is absent an abrasive coating on the remainder of the conical cutting head. Such safe zone serves as a stop for the penetration of the bur into the restorative composite material. However, further sculpting of the occlusal surface of the restored tooth is severely limited due to the geometrical configuration of the safe zone relative to the cutting head of the bur.

An occlusal cutting and sculpting device in the form of a dental bur that allows a dental practitioner who is cutting and sculpting to create an occlusal surface of restorative material formed in a repaired tooth would be a notable advance in the dental arts.

SUMMARY OF THE INVENTION

In accordance with the present application, a novel and useful occlusal cutting and sculpting device is herein provided.

The device of the present application includes a cutting head. The cutting head possesses a tapered abrasive surface that is formed by the adherence of abrasive materials such as particles of diamond, carbide, and the like. The cutting head may form into a conical member having a cuspal angle measured from the apex of the cone that mimics the cuspal angle of the natural tooth. Thus, the cutting head is tapered and includes a wide portion, a relatively narrow portion, and an intermediate portion therebetween. The relatively wide portion terminates in a first end portion while the relatively narrow portion terminates in a second end portion which may be formed into a tip. Of course, the device is used with a conventional hand piece that rotates the device to permit the cutting and sculpting.

The device of the present application is also formed with a collar. The collar overlies and connects to the first end portion of the cutting head for movement therewith. The collar is also structured with a first surface extending outwardly from and about the first end portion of the cutting head. Moreover, the collar further includes a second surface which possesses a convex radius that curves outwardly relative to the cutting head. The second surface lies apart from the cutting head and is used to serve as a rest or pivot when the cutting head is tilted to sculpt various portions of the restorative material found in the repaired tooth.

Finally, a shaft is connected to the collar and is employed with a rotating hand piece. The shaft is compatible with hand pieces of conventional construction familiar to dental practitioners.

It may be apparent that a novel and useful occlusal cutting and sculpting device for dental applications is herein provided.

It is therefore an object of the present application to provide an occlusal cutting and sculpting device for dental applications that is suitable for removing restorative material in a repaired tooth by orienting the device at various angles relative to the occlusal surface of the restorative material.

Another object of the present application is to provide an occlusal cutting and sculpting device for dental applications that provides a positive stop to avoid removal of excess restorative material during the cutting and sculpting process.

Another object of the present application is to provide an occlusal cutting and sculpting device for dental applications that is relatively easy to maneuver during use.

Another object of the present application is to provide an occlusal cutting and sculpting device that mimics the occlusal surface of a natural tooth by shaping restorative material more quickly than enamel and restorative material burs of the prior art.

Another object of the present application is to provide an occlusal cutting and sculpting device for dental applications in which the cutting head of the sculpting device is controlled due to a stop mechanism.

The application possesses other objects and advantages, especially as concerns particular characteristics and features thereof which will become apparent as the specification continues.

BRIEF DESCRIPTION OF THE SEVERAL VIEWS OF THE DRAWINGS

FIG. 5 is a side elevational view of the device of the present application sculpting contours of a tooth.

FIG. 6 is a sectional view taken along line 6-6 of FIG. 5.

FIG. 7 is a schematic top plan view of a tooth depicting cutting and sculpting areas addressed by the device of the present invention.

Figure 1:
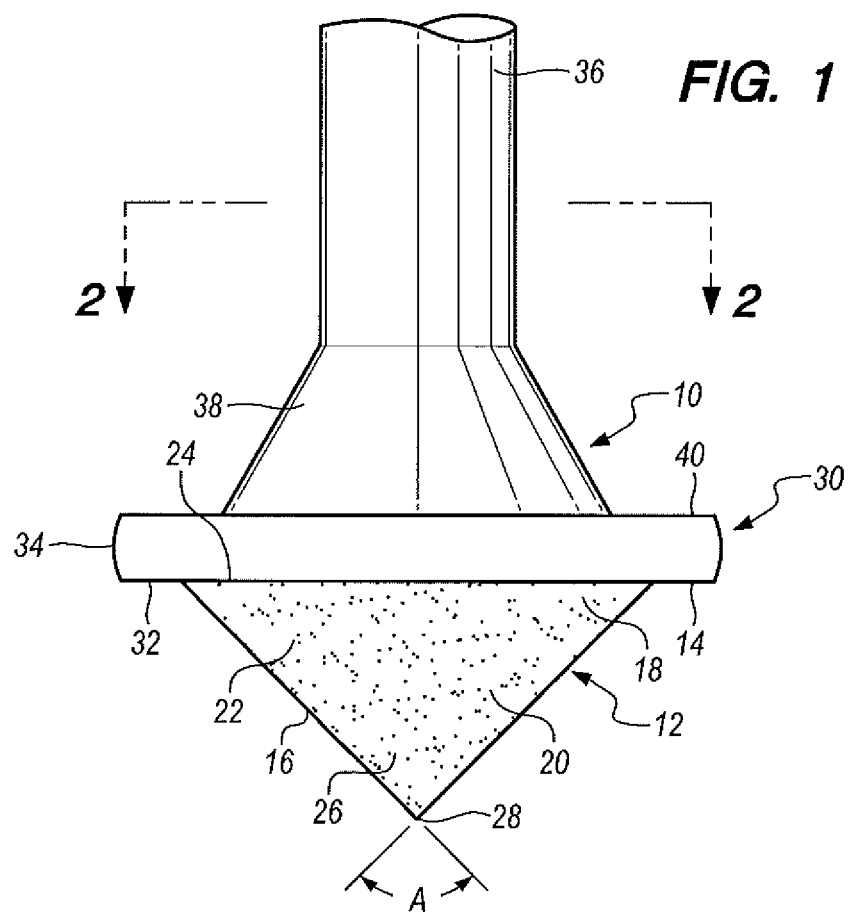
FIG. 1 is a front elevational view of the device of the present application with the shaft portion being truncated.
Figure 2:
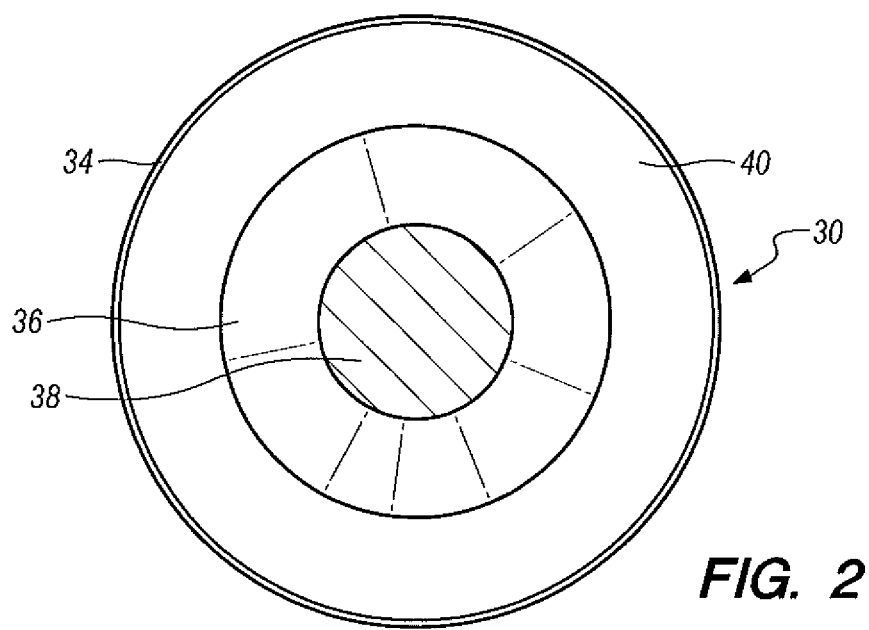
FIG. 2 is a sectional view taken along line 2-2 of FIG. 1.
Figure 3:
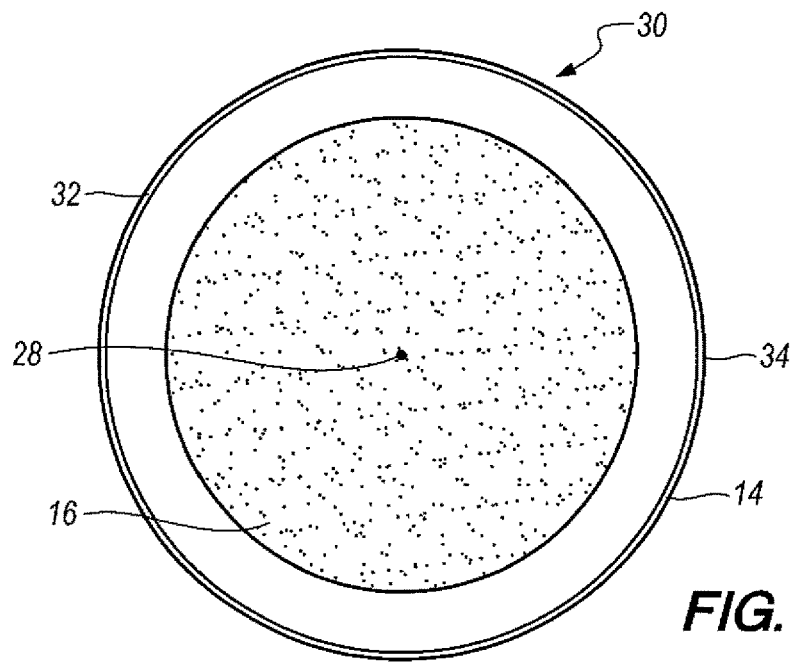
FIG. 3 is a bottom plan view of the device depicted in FIG. 1.

For a better understanding of the invention reference is made to the following detailed description of the preferred embodiments thereof which should be referenced to the prior described drawings.

DETAILED DESCRIPTION OF THE PREFERRED EMBODIMENTS

Various aspects of the present invention will evolve from the following detailed description of the preferred embodiments thereof which should be referenced to the prior delineated drawings.

The device of the present application as a whole is depicted in the drawings by reference character 10. The occlusal cutting and sculpting device 10 may also be identified as a dental bur. Device 10 is provided with a cutting head 12 which may be conical in shape. The apex angle "A" is generally between 90 and 100 degrees in order to match the natural cuspal angle of a tooth. Cutting head 12 also is provided with an abrasive surface 16 formed of diamond or carbide particles that generally range between 5 and 30 microns in size. Such particles covering abrasive surface 16 are adhered to cutting head 12 by known processes. In this regard, cutting head 12 includes a base of metallic material underlying abrasive surface 16, known in the art. Tapered abrasive surface 16 includes a relatively wide portion 18, a relatively narrow portion 20, and an intermediate portion 22 between wide portion 18 and narrow portion 20. Relatively wide portion 18 terminates in a first end portion 24 while relatively narrow portion 20 terminates in a second end portion 26. Second end portion 26 possesses a tip 28.

Most notably, device is formed with a collar 30 that overlies and connects to first end portion 24 of cutting head 12. Collar 30 is circular in configuration and also formed of metallic material. Collar 30 is further fashioned with a first surface 32 that surrounds cutting head 12. First surface 32 may be planar. Collar 30 also possesses a second surface 34 which is convex having a radius that is curved outwardly relative to cutting head 12. In other words, second surface 34 lies apart laterally, as shown in FIG. 1, from cutting head 12. First surface 32 and second surface 34 meet at edge 14.

Figure 4:
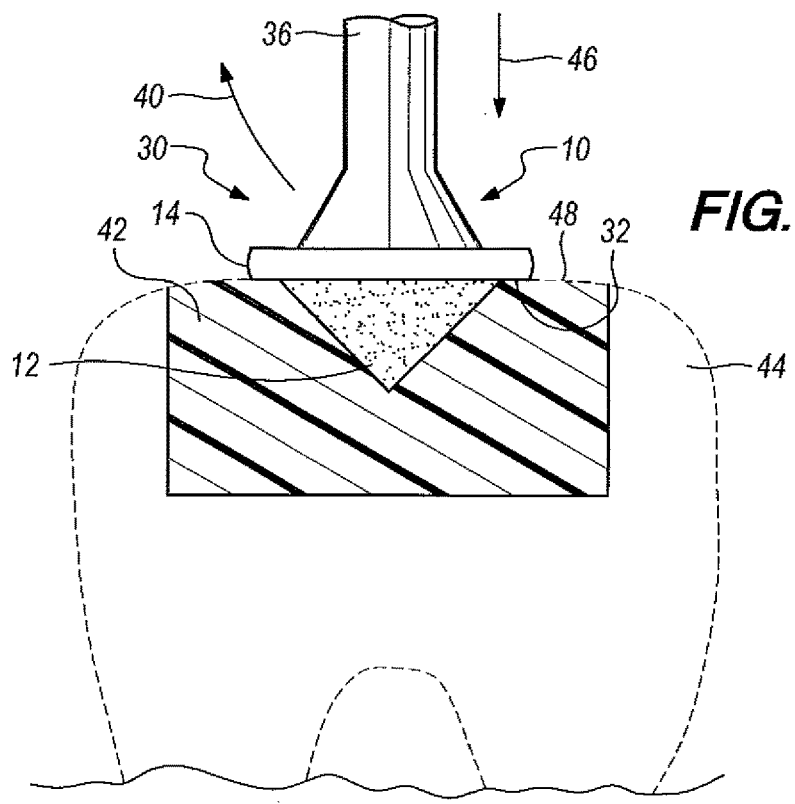
FIG. 4 is a side elevational view of the device of FIG. 1 in use on a tooth having composite restorative material in place.

Device 10 is also constructed with a shaft 36 which is shown as being truncated in FIGS. 1, 5, and 4. However, shaft 36 is generally straight and adapted to be held by a rotating hand piece normally employed by dental practitioners. Shaft 36 terminates in a flaring shoulder 38 that connects to collar 30. A surface 40 of collar 30 is formed by such interconnection between shoulder 38 of shaft 36 and collar 30. Again, shaft 36 may be formed of any suitable metallic material known in the art.

In operation, device 10 is used to cut or drill into the mass of composite material 42 depicted in section on FIG. 4 in relation to a tooth 44 shown in dashed line in the same figure. Initially, device 10 is cut or drilled downwardly according to directional arrow 46. Such cutting or drilling only proceeds as far as the contact afforded between first surface 32 or edge 14 of collar 30 and the outer surface 48 of mass of composite material 42. Thus, collar 30, specifically first surface 32 or edge 14 of collar 30, prevents or stops the further downward movement of device 10 from that depicted in FIG. 4. It should be noted that further movement of cutting head 12 of device 10 from the position shown on FIG. 4 may result in damage to the enamel of tooth 44, which is a very undesirable result. Directional arrow 48, FIG. 4, indicates the removal and rotation upwardly of device 10 following cutting or drilling downwardly according to directional arrow 46 to initiate sculpting. Referring now to FIGS. 5 and 6, it may be observed that device 10 has been tilted such that second convex surface 34 of collar 30 rests on either natural enamel or composite material found in tooth 44. It should be realized that edge 14 of device 10 may rest on enamel or composite material depending on the contour of the same. Such surface 50 is shown in dashed lines on FIG. 5. Device 10 is then able to sculpt composite material in a more lateral direction. Such further composite material is indicated by reference character 52. Such sculpting is particularly useful in forming grooves on the occlusal surface of the composite material which mimic the natural grooves found in a tooth. During this process, the convex surface 34 or edge 14 of collar 30 rests on surfaces 54 and 56 which represent enamel or composite material that has been cut by tip 28 and abrasive surface 16 of cutting head 12. With reference to FIG. 7, it may be seen that a typical drilling and sculpting procedure involves the first forming of conical pits 58, 60, and 62 in the composite material (within dashed line 72) forming the occlusal surface 64 of tooth 44. After conical pits 58, 60, and 62 are formed the practitioner moves between such pits according to the directional arrows shown on FIG. 7, resulting in the interconnection of pits and the formation of a groove therebetween. The practitioner then tilts device 10 to form grooves toward the periphery of tooth 44 per the rendition of FIGS. 5 and 6. For example, grooves 66 and 68 are shown in this regard on FIG. 7. The plurality of grooves 70 depicted on FIG. 7 follow the natural grooves found on a tooth and, thus, represent an occlusal surface of composite mass 42 possessing contours closely mimicking that of a natural tooth.

Figure 8:
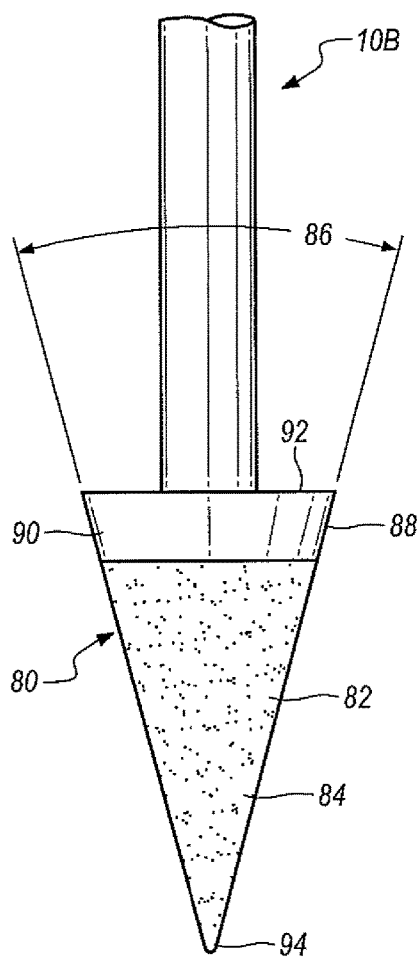
FIG. 8 is a front elevational view of another embodiment of the device of the present application, having a truncated shaft.
Figure 9:
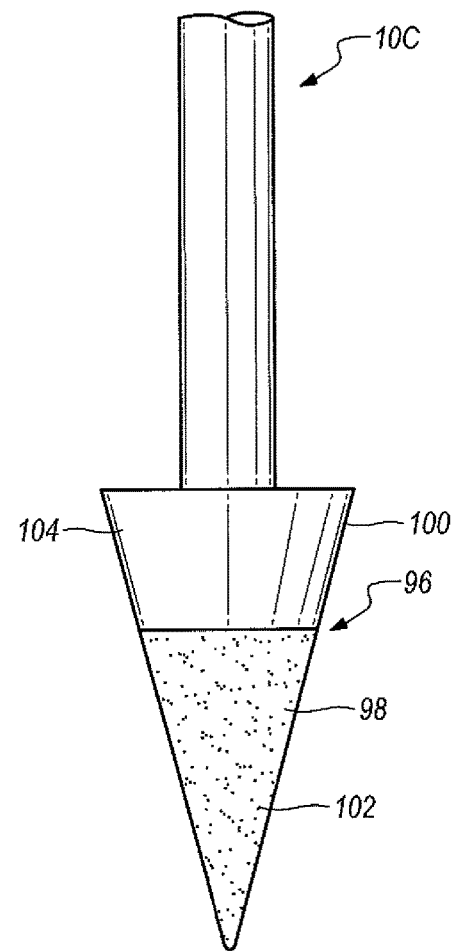
FIG. 9 is a front elevational view of yet another embodiment of the device of the present application, having a truncated shaft.

With reference to FIGS. 8 and 9, it may be observed that embodiments 10B and 10C of the present application are shown. The dental bur device 10B of FIG. 8 includes a conical body 80. Conical body 80 may be a metallic member and is divided into two zones. First zone 82 includes an abrasive surface 84 which consists of particulate hardened matter adhered to metallic member 80. Such particulate matter may take the form of finally divided diamond, carborundum, and the like. Most importantly, the apex angle 86 is relatively small compared to prior art burs. Angle 86 generally ranges between 29 and 38 degrees.

Second zone 88 has a relatively smooth surface that extends to the base 92 of conical body 80. Apex 94 forms the tip of conical body 80 at the extremely of abrasive surface 84 of first zone 82, thereof.

Referring now to FIG. 9, it may be seen that dental bur device 10C is similar to dental bur device 10B except that a conical body 96 includes a first zone 98 and a second zone 100. The abrasive surface 102 of first zone 98 includes a smaller area than abrasive surface 84 of conical body 80 of embodiment 10B. Consequently, smooth surface 104 of first zone 100 of first zone 100 of embodiment 10C is larger than smooth surface 90 of first zone 88 of embodiment 10B. It has been found that the dental bur of embodiment 10B may be used to sculpt the occlusal surface 64 of composite material 70, FIG. 7 in confined areas of tooth 44. When burs 10B or 10C are tilted as depicted in FIG. 5 with respect dental bur 10. Embodiment 10B offers more support with smooth surface 104 during the maneuver when needed.

While in the foregoing embodiments of the application have been set forth in considerable detail for the purposes of making a complete disclosure of the application it may be apparent to those of skill in the art that numerous changes may be made in such details without departing from the spirit and the principles of the application.

What is claimed is:

1. An occlusal cutting and sculpting device for dental composite material in a tooth, comprising;
    a cutting head, said cutting head further comprising a tapered abrasive surface, said cutting head including a relatively wide portion, a relatively narrow portion, and an intermediate portion between said relatively wide portion and said relatively narrow portion, said relatively wide portion terminating in a first end portion, said relatively narrow portion terminating in a second end portion, said cutting head tapered abrasive surface comprising a right circular conical body with said second end portion having a substantially pointed end tip;

a collar, said collar overlying and being connected to said first end portion of said cutting head, said collar comprising a first surface extending outwardly from and about said first end portion of said cutting head, said first surface comprising a planar surface extending away from said cutting head and positioned to stop the cutting of said cutting head, said collar further comprising a second surface, said second surface possessing a convex radius curved outwardly relative to said cutting head, said planar surface lying intermediate said cutting head and said second surface and an edge positioned adjacent said second surface, said second surface and said edge lying apart a sufficient distance from said cutting head first portion to allow said pointed end tip to sculpt dental composite material from said tooth by pivoting said cutting head about said second surface of said collar, said sculpting occurring without contact of the dental composite material on said relatively wide portion of said cutting head; and a shaft, said shaft being connected to said collar and connected cutting head via an intermediate shoulder free of abrasive material.

2. The device of claim 1 in which said conical body possesses an apex angle between 90 and 100 degrees.

3. The device of claim 1 in which said abrasive surface of said cutting head comprises diamond particles.

4. The device of claim 3 in which said diamond particles range in size between 5 and 30 microns.

\* \* \* \* \*